United States Patent [19]
Reynolds et al.

[11] Patent Number: 5,753,244
[45] Date of Patent: May 19, 1998

[54] METHOD AND PRODUCT FOR APPLYING SKIN TREATMENTS AND OINTMENTS

[76] Inventors: Taylor W. Reynolds, 2350 Maywood Dr., Salt Lake City, Utah 84109; Michael Kralik, 2508 E. Solar Dr., Holladay, Utah 84107

[21] Appl. No.: 761,386

[22] Filed: Dec. 6, 1996

Related U.S. Application Data

[63] Continuation-in-part of Ser. No. 239,964, May 9, 1994, abandoned.

[51] Int. Cl.$^6$ .................................. A61K 7/00; A61K 7/42
[52] U.S. Cl. .................................. 424/401; 424/59; 424/60; 424/70.1; 424/400

[58] Field of Search .................................. 424/59, 60, 400, 424/401, 70.1

[56] References Cited

U.S. PATENT DOCUMENTS

| | | | |
|---|---|---|---|
| 2,366,759 | 1/1945 | Thomas et al. | 424/73 |
| 2,496,270 | 2/1950 | Coler | 424/59 |
| 2,948,657 | 8/1960 | Siccama et al. | 424/63 |

*Primary Examiner*—Shelley A. Dodson
*Attorney, Agent, or Firm*—Marcus G. Theodore

[57] ABSTRACT

A method for producing and a product comprising adding an encapsulated color disappearing or color changing indicator to a topical skin lotion, spray, or other similar skin product.

8 Claims, No Drawings

METHOD AND PRODUCT FOR APPLYING SKIN TREATMENTS AND OINTMENTS

This application is a CIP of 08/239,964 filed May. 9, 1994, now abandoned.

BACKGROUND OF THE INVENTION

1. Field

This invention pertains to color changing dyes and markers for admixing with skin treatments, ointments, and other skin products to ensure uniform application to the skin for complete coverage of a desired area. Specifically, it relates to a method and product for producing a topical skin lotion, spray, or other similar skin product having color disappearing or color changing indicators which change after a short period of time after the topical product is applied to the skin.

2. State of the Art

A number of skin lotions or treatment products are transparent. These transparent skin products and treatment applications, such as suntan or skin softening lotions, are often administered haphazardly in a hit and miss fashion leaving portions of a user's skin untreated or unprotected, because a user cannot see where the transparent lotions have been applied. One solution to ensure complete skin coverage, is for a user to use opaque skin lotions or treatments which show where the skin lotion or skin treatment product has been applied. These opaque lotions or skin treatment products are not cosmetically attractive, leaving a user covered with a white or colored film. Thomas, U.S. Pat. No. 2,366,759 is an example of a brushless shaving cream in stick-like form which leaves an opaque layer for shaving purposes.

Another solution for use with transparent skin lotions or treatment products, is the admixing of permanent dyes with various skin products to indicate if a desired area of the skin has been completely coated. For example, betadine is presently admixed with local anaesthetics to ensure that a desired area of the skin is deadened with anaesthetic prior to injection or cutting. These types of admixed permanent dye anaesthetics not only stain the skin and have to be subsequently removed from the patient after surgery; but, if spilled, leave difficult to remove stains on furniture, carpets, and other fixtures.

Coler, U.S. Pat. No. 2,496,270 discloses a colorless insect repellent employing phenolphthalein and an alkaline agent which changes from red to colorless upon exposure to the atmosphere and skin acids, when applied on human skin. This indicator color change is very rapid, making it difficult to determine if the skin has been fully coated.

Of general interest is Siccama, U.S. Pat. No. 2,948,657 which is a coloring tanning agent for human skin which actually changes the color of the skin itself.

There thus remains a need for a skin treatment, ointment, or topical product which does not immediately change colors, or become transparent, after application. The method and product described below provides such an invention.

SUMMARY OF THE INVENTION

A method for manufacturing skin treatment products, ointments, sunblock, topical anesthetics, and drugs with a disappearing indicator which changes color or becomes colorless after a pre-determined period of time upon exposure to air, heat, light, or skin acid, comprises admixing with a skin treatment product, ointment, sunblock, topical anaesthetic, drug, and the like, a disappearing indicator which changes color or becomes colorless after a predetermined period of time upon exposure to air, heat, light, or skin acid. These pH indicators are admixed with the skin treatment product, ointment, sunblock, topical anaesthetic, drug, and an encapsulated acid or base which is not harmful to the skin in a decomposable coating which time releases the acid or base upon decomposition to change the indicator color or become transparent. Alternatively, the indicator may be encapsulated in a decomposable coating which releases the indicator upon decomposition to change color or become transparent upon exposure to the air or skin acidity. It has been found that without the encapsulation of the indicator or acid or base, the color or transparency change occurs too quickly during application to be of use, particularly with light sensitive indicators. With encapsulation, the timing of the color change can be adjusted by adjusting the thickness and type of coating. For example, with sunblock, the color change should occur after approximately 2–5 minutes to give a user time to apply a coating over the entire body. This is accomplished by encapsulating glycolic acid and lactic acid within an internal polysaccharide matrix and an outer polypeptide shell. An indicator, such as quinoline blue, is then added to the suntan lotion. As the suntan lotion is rubbed on or exposed to the light and heat of the sun, the encapsulated acid is released, changing the color of the indicator. By varying the thickness of the encapsulated layers, the time release rate of the indicator or acid is varied to suit the usage. For example, other products, such as anaesthetics should employ much faster color change coatings, requiring a thinner encapsulation layer.

An example of preferred encapsulation materials are the peptide delivery systems produced by Lipotec SA to entrap alpha-hydroxyacids in micro or millicapsules preventing unwanted side reactions with the rest of ingredients in a cosmetic formula. The alpha-hydroxyacids are harmless to the skin, and act as a moisturizer. The micropsheres produced by Lipotec SA under the tradename MAHA-2000 appear as a white viscous emulsion and have an oily external phase encapsulating 5% glycolic acid, 5% lactic acid in a 1% polysaccaride matrix. These micro particles are approximately 1 to 10 microns. A larger millicapsules produced by Lipotec SA under the tradename MAHA-2010 appear as red balls suspended in a gel. They have an external pH of 5.5 with a polypeptide shell encapsulating a similar glycolic acid, 5% lactic acid in a 1% polysaccaride matrix. These encapsulated alpha-hyroxyacids are added to the suntan lotion made of 3% Glucate SS, 8% Promulgen G, 1% Solulan 75, 3% Solulan 98, 1% Amerchol BL, 3% Escalol 507, 3% Glucamate SSE-20, 1% MAHA-2000, 0 to 1% Quinoline Blue, and 76L% water. The Quinoline Blue indicator changes from blue to clear after the lotion is rubbed on and the encapsulated shell breaks down releasing the alpha-hydroxyacids.

The product comprises the skin treatment product, ointment, sunblock, topical anaesthetic or drug, and the like prepared in accordance with the above method.

Examples of preferred disappearing indicators are encapsulated pH sensitive color indicators such as phenolphthalein, trimethylphenolpththalein, cyanine, etc., which change from a colored form to a clear colorless form at the pH range normally encountered on the skin. These pH indicators are added to the skin product encased in slightly alkaline colored micro capsules and then admixed with skin treatment products, such as sun block. Upon breakdown and release from the micro capsules, the encapsulated indicators change from an alkaline colored form to a colorless acidic form upon contact with the acids in skin perspiration.

Consequently, a user can see where the skin ointment or sunblock is initially applied to ensure complete coverage of the skin. After a short period of time, the acid in the skin then turns the colored indicator into a transparent form which does not have to be removed by a user. An example of a preferred sunblock is:

From 1 to 25% UV light absorber

From 74.99 to 98.9% filler

From 0.01 to 0.50% phenolphthalein encapsulated in 10 mm. microcapsules.

In another formulation, 0.01 to 0.50% thymolphthalein is used in addition to, or as a substitute for the phenolphthalein. In still another formulation, 0.01 to 0.50% cyanine is used in addition to, or as a substitute for phenolphthalein or thymolphthalein.

When these disappearing colored pH indicators are used with colorless topical disinfectants, a medical provider is assured that the disinfectant is applied to the desired skin areas before administration of a medical treatment. However, a patient does not then have to wash the stain from the treated area as is the case of betadine additives, as the colored pH indicator becomes colorless after exposure to the skin acids.

Further, in the event of accidental spillage, the colored pH indicators can be made to disappear with a mild acidic soap or cleaner, thus saving considerable clean-up expense.

An example of a preferred anaesthetic is

From 0.1 to 6% benzocaine

From 0.1 to 6% dibucaine

From 0.1% to 6% lidocaine or other anaesthetics such as salicylates, ibuprofen, acetaminophen, and other anti-inflammation medication.

0.01 to 0.5% encapsulated phenolphthalein with the remainder being a filler.

Although the above indicators are used with slightly alkaline encapsulation coatings, it is also contemplated that slightly acidic encapsulation coatings may be use. When using disappearing pH sensitive color indicators, which change from a colored form to a clear colorless form at the pH range normally encountered on the skin, these pH indicators change upon encapsulation release from the slightly acidic colored form to a colorless form upon contact with the acid pH in skin perspiration.

Topical drugs are often applied to treat skin disorders with minimal systemic side effects. Antibiotic creams or ointments are used to treat skin infections, and adrenocorticosteroids are used to treat inflammatory skin conditions. Another common dermatologic skin problem is acne, often treated with topical skin ointments and salves. Keratolytics may also be prescribed. For cosmetic and psychological reasons, preferably these topical drugs are transparent, so as not to further call attention to the user's skin problem. However, if these topical drugs are not applied to completely cover the infected area, treatment is not effective. Consequently incorporating a disappearing indicator and an encapsulated color changing reagent with the topical drug or ointment not only enables a user to ensure complete coverage, but prevents further attention from being drawn to the skin condition. An example of a preferred topical skin treatment drug for acne is:

effective amounts of treatment compound selected from the group comprising: tetracyclines, retinoic acid, isotretindin, benzoyl peroxide, and corticosteroids in desired amounts, a skin emollient filler, 0.1 to 6% phenolphthalein indicator in a slightly alkaline solution, and sufficient encapsulated alpha-hydroxyacids which, when time released, change the phenolphthalein indicator to clear.

pH or heat sensitive indicators and encapsulated reagents may be admixed with cosmetics to change from one colored form to another colored form upon contact with the acids in skin perspiration or heat. Consequently, a user can achieve rather striking cosmetic effects as the cosmetics change after a desired period of time, from one color to another. These color changing cosmetic products are particularly desirable for use with Halloween costumes or other staged events. They can also be used as party gimmicks, such as a lipstick which changes color in response to heat—i.e. a "hot lips" indicator.

An example of a preferred topical cosmetic responsive to heat is: a skin emollient base admixed with an encapsulated effective amount of the heat responsive composition selected from the group comprising $(NR_xH_{4-x})_2NiCl_4$, where $x=1,2,3$, and $(NR_{1,2,3}H_{4-1,2,3})_2NiCl_4$ wherein R is a carbon moiety group, and cholesterol ester. Upon heating, these compounds change from yellow-brown or green to blue.

Another preferred Halloween or party cosmetic employs encapsulated light sensitive indicators which may be admixed with cosmetics to change from one colored form to another colored form upon exposure to light. Consequently, a user can receive rather striking cosmetic effects as the cosmetics change from one color to another as the user emerges from a dark to a light area. A preferred topical cosmetic responsive to light is an encapsulated hair color spray which changes colors on exposure to light, such as carotene which changes from yellow to clear, for methyl red which changes from yellow to clear.

Although this specification has specifically referred to heat sensitive, pH sensitive, light sensitive, and air sensitive color indicators, any indicator with an encapsulation time color change mechanism to change colors or become transparent after a desired period of time in contact with the skin may be used. Where repeat applications of topical treatments require a certain time exposure before re-application, it is preferable to select an encapsulation material to coat the indicator which changes back from colorless to colored after a desired period of time or change in skin pH to signal the time to reapply the medication or topical treatment.

The invention thus provides a method for producing a skin treatment, ointment, or topical product which changes colors, or becomes transparent, after topical application.

Although this specification has made reference to the illustrated embodiments, it is not intended to restrict the scope of the appended claims. The claims themselves recite those features deemed essential to the invention.

We claim:

1. A method for manufacturing skin treatment products, ointments, sunblock, topical anesthetics, and drugs comprising:

admixing with the skin treatment product, ointment, sunblock, topical anaesthetic, and drugs,
   i. an indicator which changes color or becomes transparent upon release and exposure to the air, heat, lights or skin acidity, encapsulated in a time delayed decomposable coating of a thickness selected to time delay release of said indicator to change color or become transparent after a desired time period;
   ii. said indicator and decomposable coating of a chemical composition and concentration which do not react with or irritate the skin.

2. A method for manufacturing skin treatment products, ointments, sunblock, topical anesthetics, and drugs according to claim 1, wherein the indicator is a pH indicator.

3. A method for manufacturing skin treatment products, ointments, sunblock, topical anesthetics, and drugs according to claim 1, including an encapsulated indicator reactive reagent in a time delayed decomposable coating which changes the color or transparency of the indicator upon release and contact with the indicator, said indicator and reagent of a chemical composition and concentration which do not react with or irritate the skin.

4. A method for manufacturing skin treatment products, ointments, sunblock, topical anesthetics, and drugs according to claim 1, wherein the encapsulating coating comprises an inner polysaccharide matrix and an outer polypeptide shell.

5. A product comprising a skin treatment product, ointment, sunblock, topical disinfectant, anaesthetic, and drug, prepared in accordance with claim 1.

6. A method according to claim 3, wherein the disappearing indicator is quinoline blue, and the reagent is an alpha hydroxyacid selected from the group comprising glycolic, lactic, citric, and lactic acids encapsulated in a polypeptid millicapsule shell of desired thickness.

7. A method for manufacturing skin treatment products, ointments, sunblock, topical anesthetics, according to claim 1, wherein:

the indicator is an effective amount of heat responsive composition selected from the group comprising $(NR_xH_{4-x})_2NiCL_4$, where x=1, 2, 3, and $NR_{1,2,3}H_{4-1,2,3})_2NiCl_4$, wherein R is a carbon moiety group which changes from yellow to brown or green to blue upon exposure to heat; and carotene which changes from yellow to clear upon exposure to heat, and methyl red which changes from yellow to clear upon exposure to heat.

8. A product comprising a skin treatment product, ointment, sunblock, topical disinfectant, anaesthetic, and drug prepared in accordance with the method of claim 7.

* * * * *